United States Patent
Tsuchiya

(10) Patent No.: US 10,145,791 B2
(45) Date of Patent: Dec. 4, 2018

(54) ELECTRIC FIELD IMAGING METHOD

(71) Applicant: NATIONAL INSTITUTE OF INFORMATION AND COMMUNICATIONS TECHNOLOGY, Tokyo (JP)

(72) Inventor: Masahiro Tsuchiya, Tokyo (JP)

(73) Assignee: NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 0 days.

(21) Appl. No.: 15/559,906

(22) PCT Filed: Jan. 27, 2016

(86) PCT No.: PCT/JP2016/053118
§ 371 (c)(1),
(2) Date: Sep. 20, 2017

(87) PCT Pub. No.: WO2016/152257
PCT Pub. Date: Sep. 29, 2016

(65) Prior Publication Data
US 2018/0095037 A1    Apr. 5, 2018

(30) Foreign Application Priority Data

Mar. 23, 2015 (JP) ................................. 2015-059072

(51) Int. Cl.
*G01N 21/552* (2014.01)
*G01R 29/08* (2006.01)
*G01N 21/64* (2006.01)

(52) U.S. Cl.
CPC ......... *G01N 21/552* (2013.01); *G01N 21/648* (2013.01); *G01R 29/08* (2013.01)

(58) Field of Classification Search
CPC ........................ G01N 21/552; G01N 21/648
(Continued)

(56) References Cited

U.S. PATENT DOCUMENTS

2018/0106724 A1* 4/2018 Wang ..................... G01R 29/00

FOREIGN PATENT DOCUMENTS

| JP | 05-307057 A | 11/1993 |
| JP | 06-209910 A | 8/1994 |
| JP | 10-221391 A | 8/1998 |

OTHER PUBLICATIONS

Kiyotaka Sasagawa et al., "Live Electrooptic Imaging System Based on Ultraparallel Photonic Heterodyne for Microwave Near-Fields", IEEE Transactions on Microwave Theory and Techniques, Dec. 10, 2007, pp. 2782-2791, vol. 55, No. 12.
(Continued)

*Primary Examiner* — Roy M Punnoose
(74) *Attorney, Agent, or Firm* — Sughrue Mion, PLLC

(57) ABSTRACT

To minimize or prevent obstruction by a surface-mounted part or disturbance to an object to be visually observed, an electric field sensor is placed at a predetermined distance from a surface of the object to be visually observed, and a two-dimensional distribution of a high-frequency electric field is detected. Considering that the measured electric field distribution is due to an electrostatic field from the electric field distribution at the surface of the visually observed object, the electric field distribution at the surface is back-calculated from Gauss' flux theorem or the like, and the obtained electric field distribution is displayed or outputted. Thus, the electric field distribution at a position closer to the surface of the visually observed object is imaged while obstruction by a surface-mounted part or disturbance to the visually observed object is suppressed.

7 Claims, 7 Drawing Sheets

(58) Field of Classification Search
USPC .......................................................... 356/369
See application file for complete search history.

(56) References Cited

OTHER PUBLICATIONS

Masahiro Tsuchiya et al., "Detached electrooptic imaging (DEI)", Applied Physics Express, 2015, pp. 042502-1-042502-4, vol. 8, No. 4.
M. Tsuchiya et al., "Photonics Makes Microwaves Visible", Research Highlights, IEEE Photonics Society Newsletter, Dec. 2012, pp. 9-17, vol. 26, No. 6.
International Search Report for PCT/JP2016/053118, dated Apr. 12, 2016.

* cited by examiner (a)

(b)

ELECTRIC FIELD IMAGING METHOD

CROSS REFERENCE TO RELATED APPLICATIONS

This application is a National Stage of International Application No. PCT/JP2016/053118 filed Jan. 27, 2016 (claiming priority based on Japanese Patent Application No. 2015-059072 filed Mar. 23, 2015), the contents of which are incorporated herein by reference in their entirety.

TECHNICAL FIELD

The present invention relates to an electric field imaging method for visually observing in real time a spatial evanescent field distribution of a high-frequency signal in an electronic circuit or the like.

BACKGROUND ART

Visually observing a spatial distribution of a high-frequency signal of a circuit in real time and intuitively grasping an outline of the operation thereof. This is a function leading to essential innovation, and a method for implementing the function is very attractive from academic and technological viewpoints. Use of the function in various fields, for example, analysis or diagnosis of a high-speed electronic circuit or an advanced antenna, suppression of EMI, and so forth, is expected.

The unique means for visualizing the spatial distribution of the high-frequency signal in real time is the live electrooptic imaging technique, which has been invented by NICT (National Institute of Information and Communications Technology). With this live electrooptic imaging camera, in which ultra-parallelism and ultrahigh speed of light are used in a superimposed manner through the electrooptic effect, an electric field distribution in a microwave band up to 100 GHz can be imaged and displayed in real time.

Various techniques for imaging an electric field distribution have been proposed or realized, excluding a condition "imaging and displaying in real time". In these techniques, electric fields around various electronic circuits or electronic apparatuses are imaged although spatial scanning takes a long time, and intuitive analysis is applied. Therefore, demands for a real-time imaging technique are high.

CITATION LIST

Non Patent Literature

NPL 1: M. Tsuchiya and T. Shiozawa, "Photonics makes microwaves visible", Research Highlights, IEEE Photonics Society Newsletter, Vol. 26, Number 6, December 2012, pp. 9-17

SUMMARY OF INVENTION

Technical Problem

A point to be improved in the conventional electric field imaging technique is that it is necessary to cause an electrooptic crystal serving as a sensor head and a planar circuit to be in close contact with each other. This is a requirement to prevent degradation of a spatial resolution, but degrades non-invasiveness at the time of observation.

Furthermore, in a case where electronic parts having finite heights are mounted on a circuit board surface or in a case where electrodes are embedded in the circuit board surface, the close contact between the circuit and the electrooptic crystal is hindered. In particular, in a case of an electrooptic crystal plate for shortening an imaging time by avoiding mechanical two-dimensional scanning, the electrooptic crystal plate is relatively large and thus such close contact is impossible to achieve in many cases. On the other hand, in a case of performing mechanical two-dimensional scanning, a complicated operation is required to insert a sensor between parts, and the insertion is impossible in some cases. Furthermore, invasiveness may increase.

In such a case, imaging is performed with a bottom surface of the electrooptic crystal or a two-dimensional scanning surface being kept at a finite height from the circuit surface. In this case, however, a spatial resolution in a lateral direction may degrade and it may be impossible to obtain a sufficient spatial resolution in the lateral direction. The degradation of a spatial resolution for an evanescent electric field from a circuit pattern on the substrate surface results from its expansion in the lateral direction as the height increases. That is, imaging is performed in a so-called out-of-focus state.

Solution to Problem

An electric field imaging method according to the present invention is a method for detecting and imaging a two-dimensional distribution of a high-frequency evanescent electric field from a high frequency circuit as an object to be visually observed (hereinafter abbreviated as a high-frequency electric field distribution), by using an electric field imaging apparatus including an electric field sensor, a sensor signal processing unit, an image signal processing system, and display means, including:

(1) detecting, by using the electric field sensor, a high-frequency electric field distribution at a position a predetermined distance away from a surface of the object to be visually observed;

(2) processing, by using the sensor signal processing unit, a signal from the electric field sensor to convert the signal to an image signal;

The high-frequency electric field distribution at the surface obtained in (3) may be resolved into a spatial frequency spectrum after multiplied by a predetermined window function, filtered using a spatial spectrum filter having a predetermined filtering characteristic, and subjected to inverse Fourier transform so that a predetermined spatial frequency filtering may be carried out.

It is desirable that the spatial spectrum filter has, at least at a high-frequency end, a spectrum reduction rate higher than an average in the spatial frequency spectrum. It may be desirable to reduce a spectrum at a specific spatial frequency as well as at the high-frequency end.

Advantageous Effects of Invention

In measurement of an electric field at a surface of an object to be visually observed, a high-frequency electric field distribution at a position closer to the object to be visually observed relative to the detection position of the electric field sensor or at a position corresponding to the surface of the object to be visually observed can be imaged while performing observation from a position slightly away from the surface and suppressing disturbance to the object to be visually observed.

DESCRIPTION OF EMBODIMENTS

Figure 1:
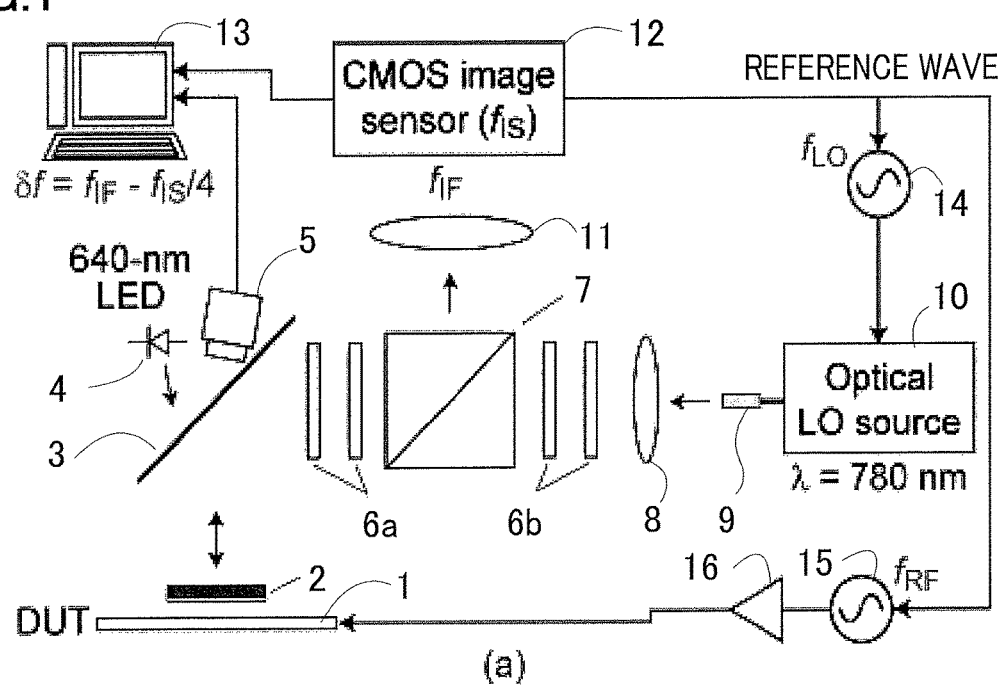
FIG. 1(a) is a diagram illustrating an example of an apparatus to which an electric field imaging method according to the present invention can be applied, and (b) is a diagram illustrating a cross-section of an electric field sensor 2 together with an example of a holding mechanism.
Figure 1:
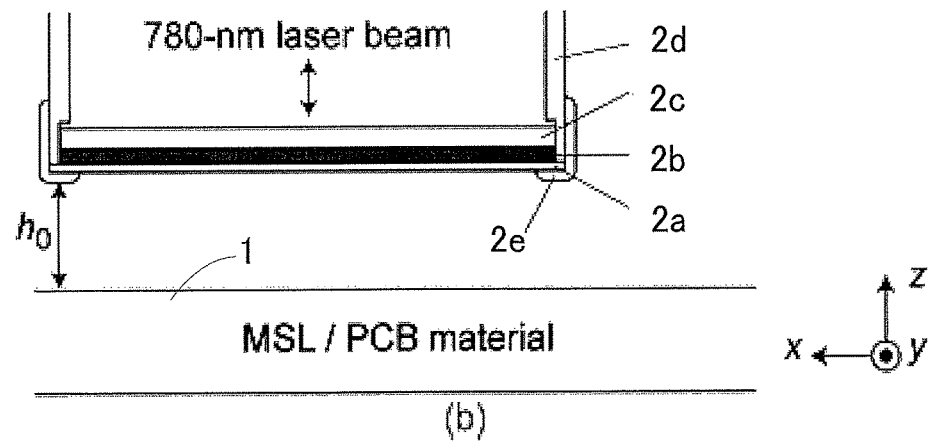

Hereinafter, an embodiment of the present invention will be described in detail on the basis of the drawings. In the following description, apparatuses having identical functions or similar functions are denoted by identical reference numerals when there is no special reason.

FIG. 1 illustrates an example of an apparatus to which an electric field imaging method according to the present invention can be applied. In an live electrooptic imaging camera illustrated in FIG. 1(a), an electric field sensor 2 using an electrooptic crystal plate is detached immediately above a planar circuit which is an object to be visually observed 1 as an observation target. A distribution of change in a refractive index occurs in the electrooptic crystal plate in accordance with a distribution of an evanescent electric field from the circuit operating at a frequency $f_{RF}$. The change in the refractive index is detected by using a laser light beam that has been modulated by an LO (local oscillation) frequency $f_{LO}$ of a local oscillator 14 and emitted by an optical LO source 10, and at the same time frequency conversion occurs. Finally, a laser beam including an intensity modulation distribution of an IF (intermediate f frequency: $f_{IF}=f_{RF}-f_{LO}$) signal is generated, the laser beam is received by an image sensor 12 (high-speed CMOS (complementary metal-oxide-semiconductor) image sensor) (IS, reading frequency $f_{IS}$), signal processing is performed thereon by a computer 13 that includes a signal processing unit and a display unit, and a high-frequency electric field distribution image is displayed in real time.

FIG. 1(b) illustrates in detail a cross-section of the electric field sensor 2 together with an example of a holding mechanism. In this example, an element formed by providing a sapphire layer 2a (having a thickness of 0.2 mm) on an object to be visually observed side of an electrooptic crystal plate 2b composed of ZnTe (having a thickness of 0.35 mm) and providing a quartz crystal layer 2c (having a thickness of 0.5 mm) on a laser beam side of the electrooptic crystal plate 2b, is held by a polyacetal holder 2d by using a polyimide tape 2e (having a thickness of 0.07 mm).

Figure 2:
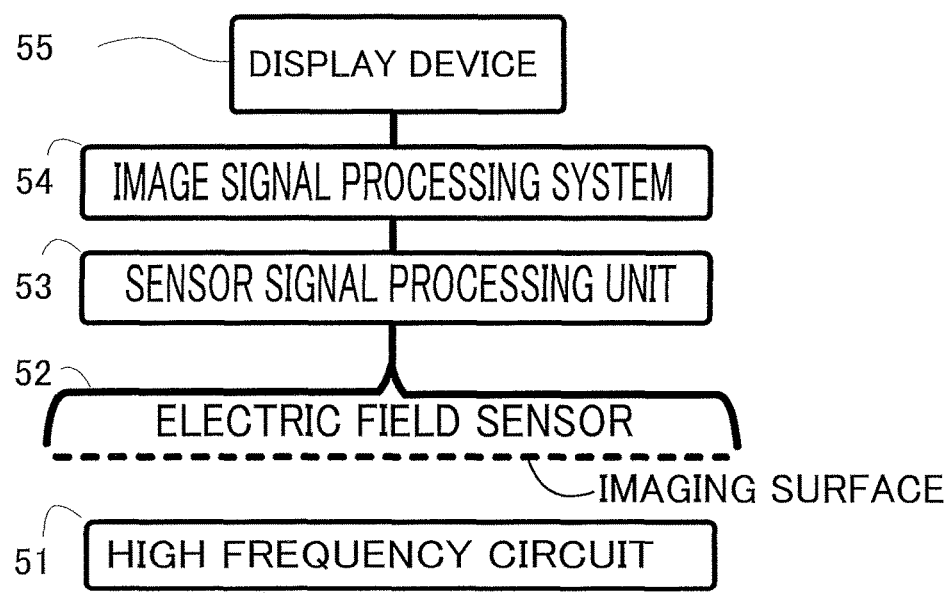
FIG. 2 is a block diagram of an apparatus as a target of the present invention.

FIG. 2 is a block diagram of an apparatus to which the present invention is applied, specifically, a block diagram of an electric field imaging apparatus including an electric field sensor 52, a sensor signal processing unit 53, an image signal processing system 54, and a display device 55. A two-dimensional distribution of a high-frequency electric field emanating from a high frequency circuit 51, which corresponds to the objet to be visually observed 1, is detected by using this apparatus. Regarding the correspondence to FIG. 1(a), the electric field sensor 52 corresponds to the electric field sensor 2, the sensor signal processing unit 53 corresponds to an optical system for detecting a change in polarization, that is, an optical system and devices located on a path of light emitted by the laser light source, passing through a polarization beam splitter 7, subjected to polarization modulation by the electric field sensor 2, reflected, and passing through the polarization beam splitter 7 to reach the image sensor 12, and the image signal processing system 54 and the display device 55 correspond to the computer 13.

FIG. 2 illustrates an example of an electric field imaging apparatus, but a magnetic field imaging apparatus for imaging a magnetic field distribution can be used in the present invention. In this case, a magnetic field sensor is used, and a sensor signal processing unit converts a signal from the magnetic field sensor to an image signal of a magnetic field distribution at a surface.

Furthermore, FIG. 2 illustrates an example in which a high-frequency electric field distribution is obtained almost collectively by the image sensor 12. However, it is already well known that scanning with a small electric field sensor enables imaging of a high-frequency electric field distribution in a region having a larger area than the small electric field sensor.

Figure 3:
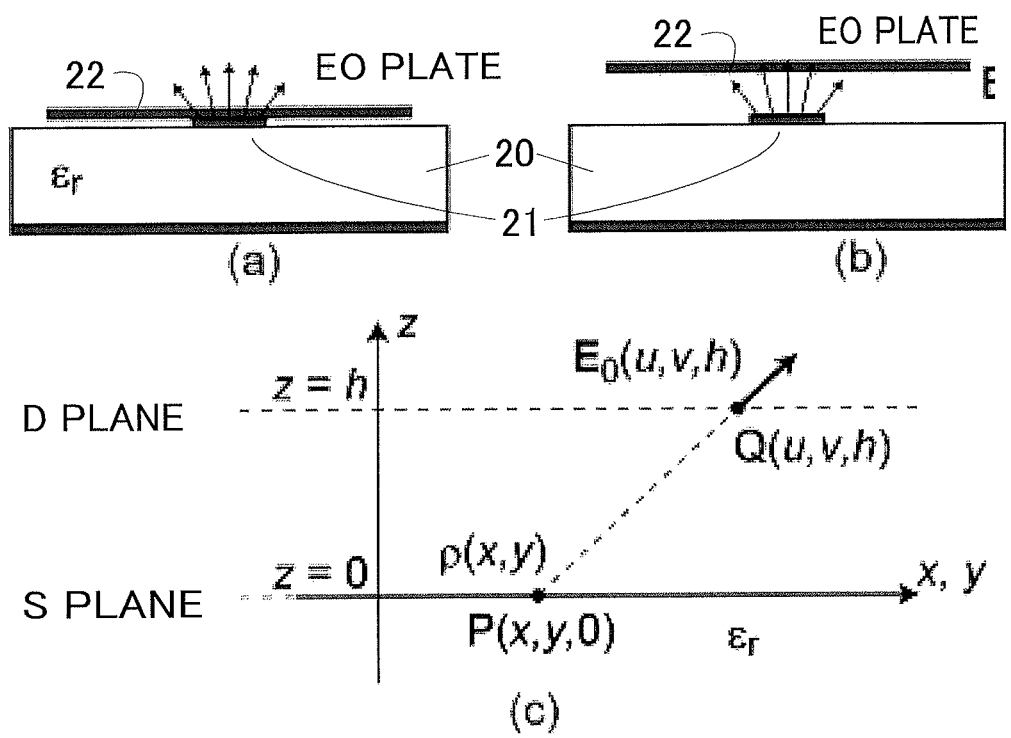
FIG. 3 is a diagram illustrating (a) a case of observation with a close-contact live electrooptic imaging camera and (b) a case of observation with a non-close-contact live electrooptic imaging camera regarding a position of an electrooptic crystal plate and illustrates, for analyzing the cases, (c) a relationship between electric charge at a substrate surface and an electric field thereabove. In a case of two-dimensional scanning, the electrooptic crystal plate corresponds to a scanning surface.

Here, a microstrip line 21 is used as the planar circuit, which is an observation target (FIG. 3). It is obvious that a maximum spatial resolution is obtained in this measurement system under a state where a bottom surface of an electrooptic crystal plate 22 is in close contact with an upper-surface electrode of the microstrip line 21 (FIG. 3(a)). In contrast to this, it is assumed in the present invention that the electrooptic crystal plate is away from the upper-surface electrode by h, as illustrated in FIG. 3(b).

<Principle>

First, an electromagnetics model illustrated in FIG. 3(c) is discussed. It is assumed that a space where z<0 is filled with a dielectric body having a relative permittivity $\varepsilon_r$, and that an electric charge distribution ρ (x, y) exists on an xy plane where z=0. It is assumed that ρ (x, y) is defined by the planar circuit and an electric signal. Now, attention is focused on one point P (x, y, 0) on the xy plane and another point Q (u, v, h) above at h. According to the electromagnetics, an electric field $E_0$ generated at the point Q by the electric charge distribution ρ (x, y) at the point P is in the direction of a straight line PQ and is expressed by the following expression, in which $\varepsilon_0$ represents a permittivity of vacuum.

$$\vec{E}_0(u, v, x, y) = \frac{\rho(x, y)}{2\pi r^2 \varepsilon_0 (1 + \varepsilon_r)} \vec{e}$$ [Math. 1]

$$r\vec{e} = (u - x, v - y, h)$$

$$r = \sqrt{(u-x)^2 + (v-y)^2 + h^2}$$

In an electric field vector generated through contribution of all electric charge on a substrate surface (S plane), a value E (u, v, h) at the point Q is given as an area in the xy plane in the above expression, and obtains the following relation.

$$\vec{E}(u, v, h) = \iint_{-\infty}^{\infty} dx dy \, \vec{E}_0(u, v, x, y, z=h)$$ [Math. 2]

When an attention is focused on an electric field component $E_Z$ in a z direction, it can be expressed as follows. Here, * represents a convolution operation.

$$E_z(u, v, h) = \left[\frac{\rho(x, y)}{2\pi \varepsilon_0 (1 + \varepsilon_r)}\right] * \left[\frac{h}{(x^2 + y^2 + h^2)^{1.5}}\right] \equiv a * b$$ [Math. 3]

Focusing on the above expression being a convolution integral regarding a and b, a multiplication relation in the Fourier space is used to obtain the following expression.

$$\rho(x, y) = 2\pi \varepsilon_0 (1 + \varepsilon_r) \mathcal{F}^{-1}\left(\frac{\varepsilon_z}{B}\right)$$ [Math. 4]

$\varepsilon_Z$ and B represent $E_Z$ and b that have undergone Fourier transform, respectively. F and $F^{-1}$ represent Fourier transform and inverse Fourier transform, respectively.

Here, Gauss' law (Gauss' flux theorem) is applied to the xy plane (S plane) where z=0, thereby obtaining the following expression.

$$E_z(x, y, 0) = \frac{\rho(x, y)}{\varepsilon_0(1 + \varepsilon_r)} = 2\pi \mathcal{F}^{-1}\left\{\frac{\mathcal{F}[E_z(x, y, h)]}{B}\right\}$$ [Math. 5]

With this expression, an $E_Z$ image on the S plane is obtained on the basis of an $E_Z$ image on the D plane. This is the principle of this method.

The description of the principle given above relates to a method of performing inverse Fourier transform by preforming division in the Fourier space. The same result can be obtained by performing deconvolution on E (x, y, h) by using a result obtained by performing inverse Fourier transform on 1/B. In the present invention, processing may be performed by using any of these methods in principle, but it is desired to adopt a method insusceptible to a rounding error or the like in data processing.

A frequency range to which this principle can be applied is considered to be determined by an upper limit of a time period in which an evanescent electric field propagates a distance r because Expression 5 is a relational expression in an electrostatic field. It is necessary to examine the propagation speed of the evanescent electric field for further examination.

<Procedure of Imaging Process>

Figure 4:
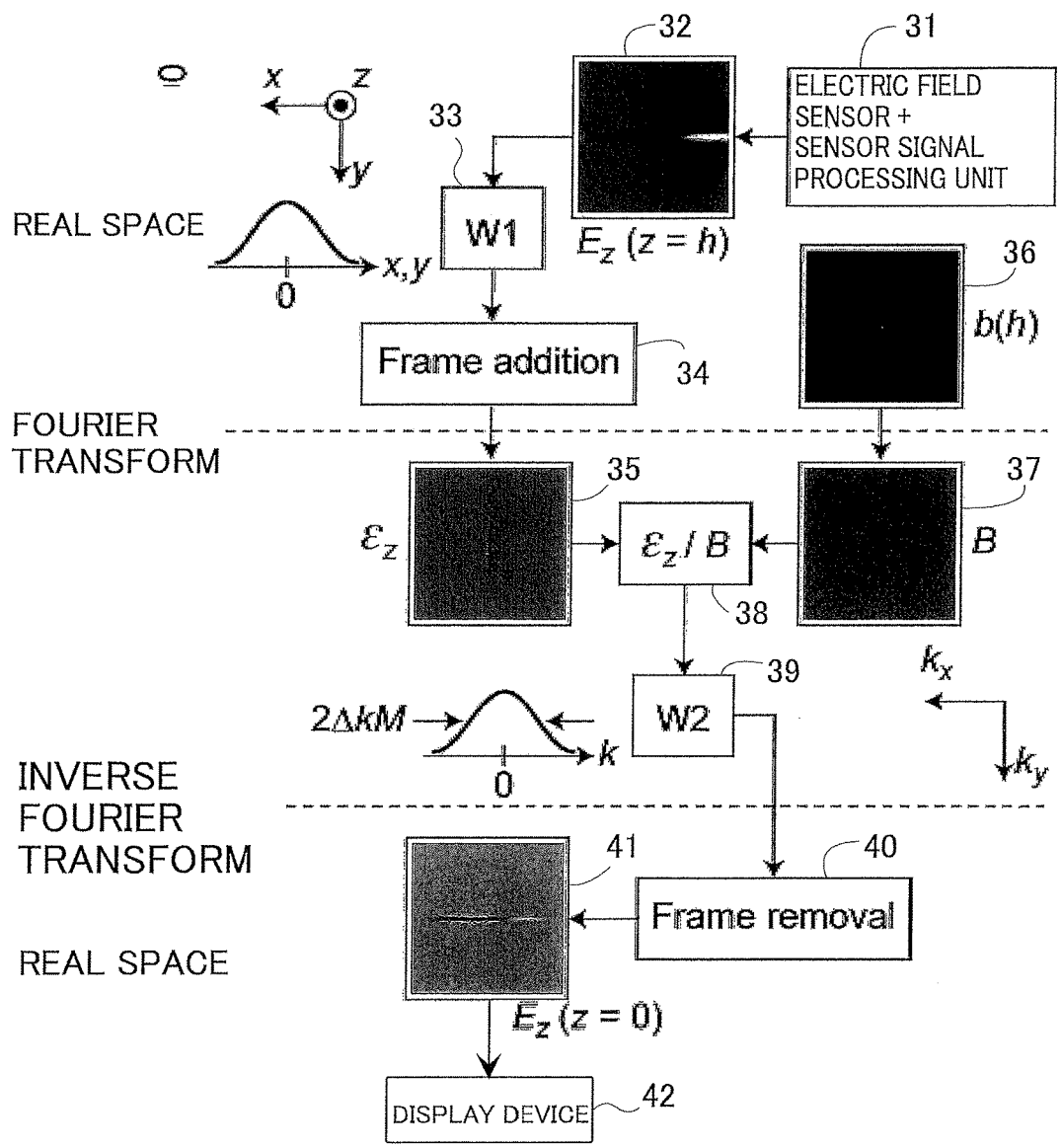
FIG. 4 is a flowchart illustrating a flow of an example of a process based on the principle according to the present invention (here, an example of a DEI (detached electrooptic imaging) process in which an electrooptic crystal plate is used as a sensor).

FIG. 4 is a flowchart illustrating a flow of a process according to the above-described principle (DEI process). First, an electric field sensor+sensor signal processing unit (31) obtains an LEI image. It is assumed that an $E_Z$ image (32) in z=h is a complex phasor video image including phase information. The number of pixels and the interval of pixels are, for example, 100×100 and 0.25 mm of the live electrooptic imaging camera, respectively. It is desirable that the number of pixels of the live electrooptic imaging camera be larger, and that the interval of pixels be small in general. When FFT (fast Fourier transform) is performed on a 100×100 image obtained accordingly, if surrounding pixels have a finite value, noise resulting from discontinuity occurs. Thus, a raised-cosine window function W1 (33) is used, for example. Other various window functions are known, and any window function capable of suppressing the occurrence of noise may be selected and used.

For example, an FFT plug-in of image processing software ImageJ can be used for Fourier transform (34) in this case (Image) is an open-source image processing program for multidimensional images in the scientific field). The same applies to a b function (36). A pixel interval Δk in a Fourier space (37) is given as 2π/Δ×N (for example, N=128). In some of other types of Fourier transform software, a value other than the power of 2 can be set as a value of N of Fourier transform or inverse Fourier transform.

As a result of division by B (38) in the Fourier space, an excessive noise component may be generated in a component having a high spatial frequency. To suppress this, for example, a raised-cosine window function W2 (39) is used. In some cases, it is desirable to reduce a spectrum at a specific spatial frequency as well as at a high-frequency end. Also in this case, various window functions are known, and any window function capable of suppressing the occurrence of noise may be selected and used. The number of pixels corresponding to the half width at half maximum of the window function is represented by M. For example, the FFT function of ImageJ can be used for inverse Fourier transform (40). As a result, a DEI image in h=0 (41) is obtained.

<Verification Through Simulation>

To verify the above-described principle, the principle was applied to a result of numerical simulation. The numerical simulation, in which both $E_Z$ (Z=0) and $E_Z$ (Z=h) can be grasped, is useful to minutely examine an effect of application of the principle.

Figure 5:
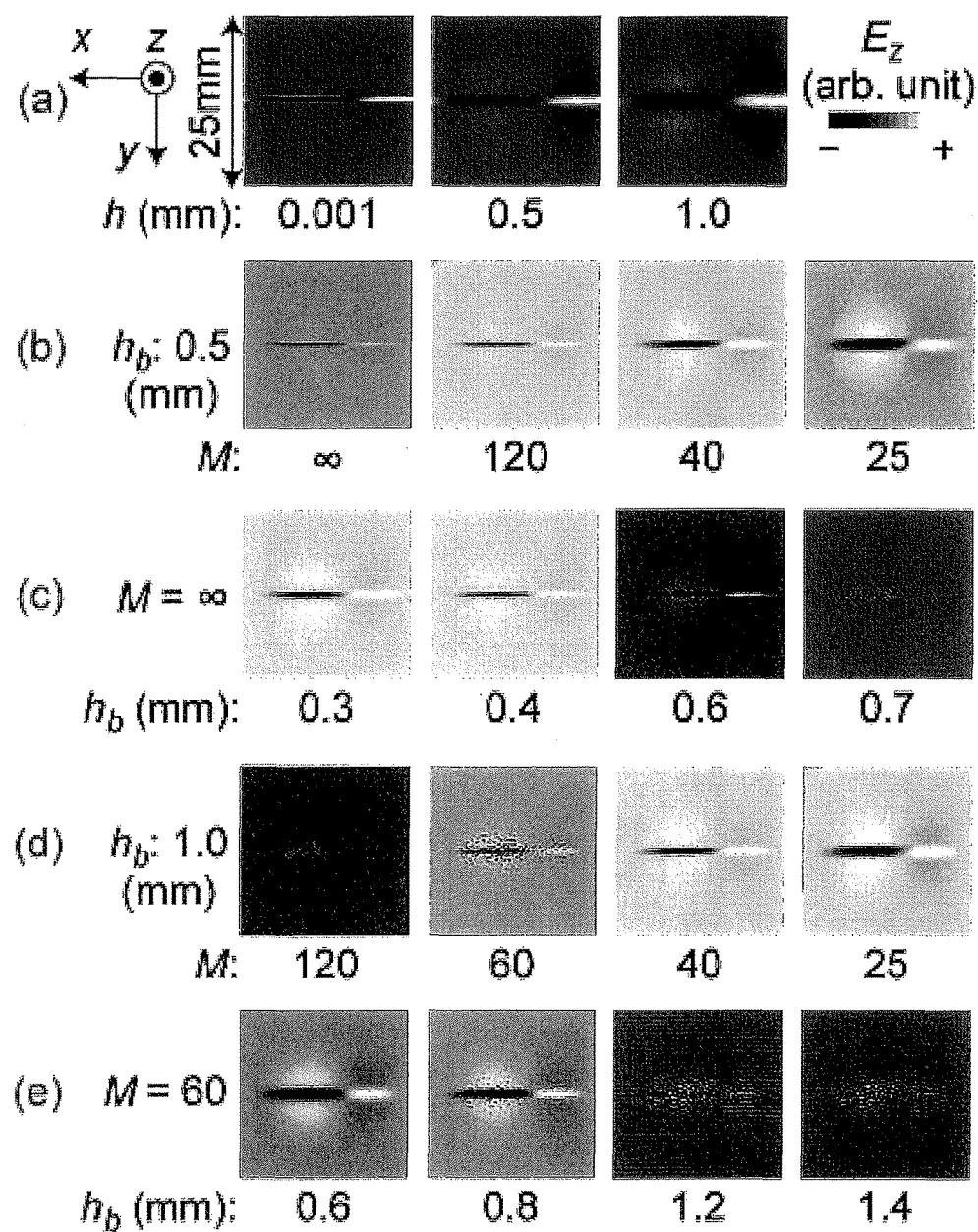
FIG. 5 illustrates a result of applying a DEI process to high-frequency electric field images obtained through simulation. (a) illustrates real parts of complex exponent display in cases where h is 0.001, 0.5, and 1.0 mm; (b) and (c) illustrate a result of DEI at a height h of 0.5 mm; and (d) and (e) illustrate a result of DEI at a height h of 1.0 mm and correspond to the case (a), M corresponding to a half width at half maximum of a window function W2 (FIG. 4) expressed by the number of pixels.

Specifically, a model was assumed in which a 6 GHz signal is caused to propagate from the right to the left through a microstrip line having a line width of 0.3 mm and formed on an FR4 substrate having a thickness of 1.6 mm (that is, a line on a glass epoxy substrate), and an electromagnetic field distribution above the substrate was obtained by using a general-purpose electromagnetic field simulator HFSs. "h" was 0.5 mm and 1.0 mm. An $E_Z$ distribution as a result thereof is illustrated in FIGS. 5(a) and (c) (note that (a) and (c) illustrate only real parts of complex electric field phasor video images, multiplied by a window function W1). Here, note that the electric field video images are displayed in an 8-bit grayscale but the brightness and contrast are automatically adjusted by an algorithm of the image software ImageJ. In these figures, the distribution widths of the microstrip line images are apparently larger than the above-described line width, and the full widths at half maximum thereof are 0.88 mm and 1.37 mm.

<M Dependence of Spatial Resolution>

Figure 6:
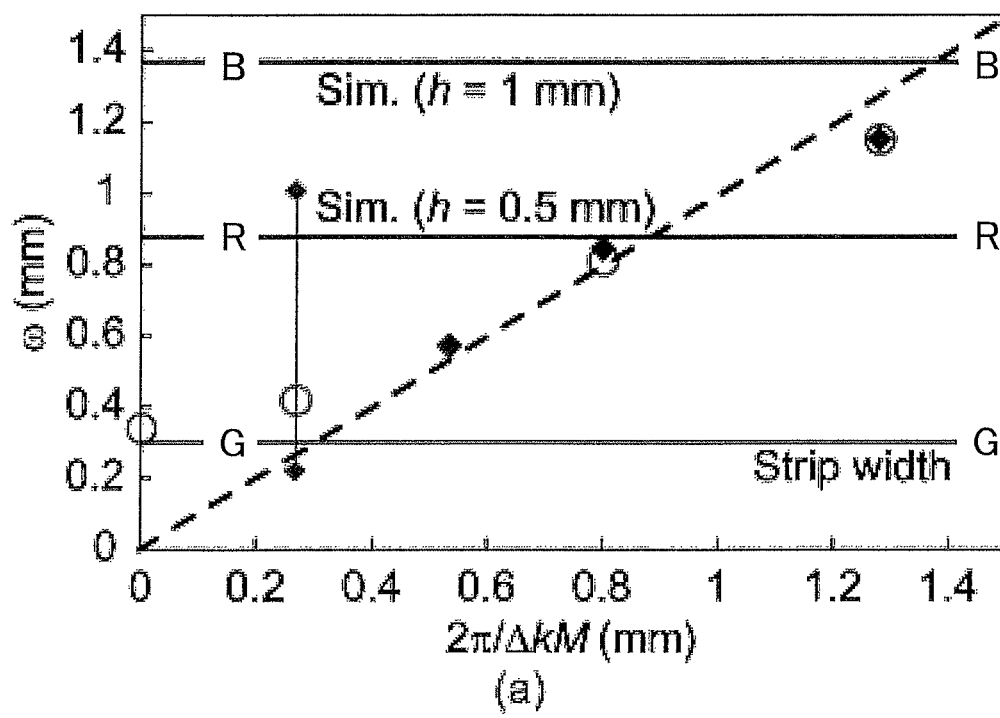
FIG. 6 illustrates an electric field distribution width (FWHM) in the DEI result in FIG. 5, in which (a) illustrates dependence of the window function W2 on a reciprocal of the width M, and a broken line represents the width of uncertainty determined by M. (b) B illustrates dependence of a function on an h value, and a broken line represents the width of uncertainty determined by M=60. ○ and ♦ respectively represent the DEI results at heights of 0.5 mm and 1.0 mm, a solid line R and a solid line B represent electric field distribution widths in respective simulation results, and a solid line G represents a microstrip line width.
Figure 6:
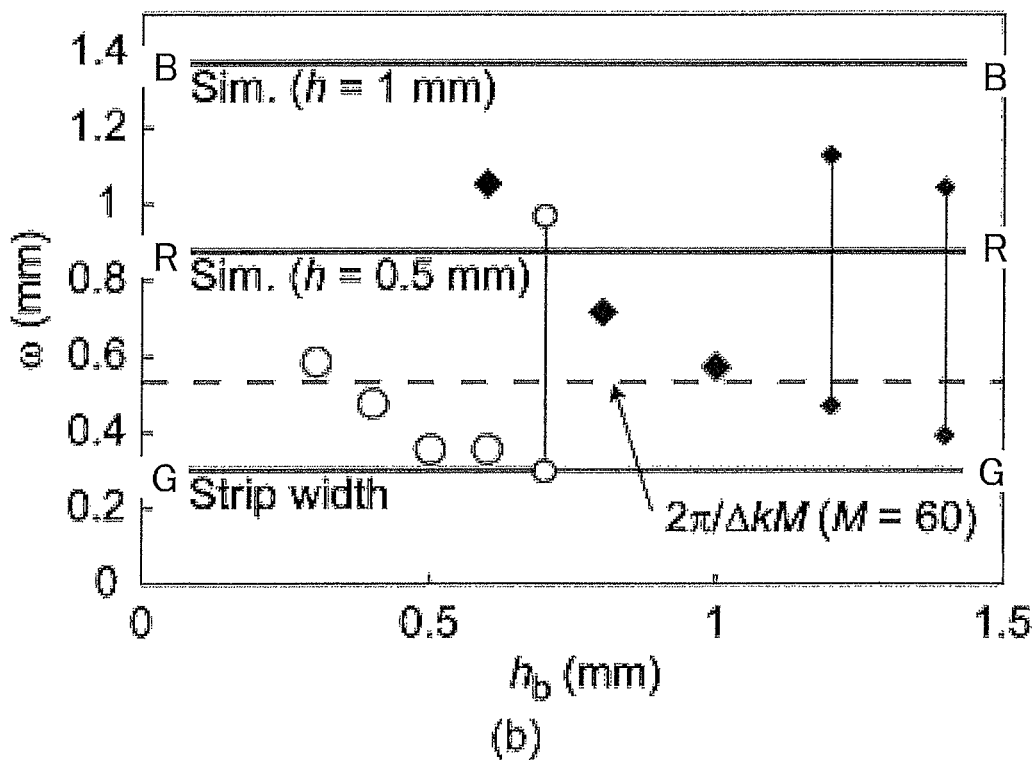

First, M (full width at half maximum) dependence of a spatial resolution in a case where h=0.5 mm was examined regarding h in Expressions 1 to 6. The result is illustrated in FIG. 5(a) and FIG. 6(a). It is considered that, in a case where M is infinity, that is, in a case where a window function is not used, a sufficiently high spatial resolution is exhibited although there is slight noise superimposition. The distribution width in a vertical direction (FWHM) can be read as 0.34 mm. This value is approximate to 0.3 mm, which is the width of an upper electrode of the microstrip line, and is within a quantization error in consideration of a pixel interval of 0.25 mm. Accordingly, the principle can be regarded as being almost verified.

On the other hand, a decrease in M causes an increase in the distribution width (FWHM) on the image. The distribution width may exceed the distribution width before the process. This is because a window function limits a high-frequency component in the Fourier space. Actually, FIG. 6(a) illustrates a tendency in which the distribution width increases in proportion to 1/M. A case where M=25 is exceptional, but the cause thereof is unknown at the present (not the influence of a decrease in the line width caused by W1).

A result of similarly examining M dependence in a case where h=1.0 mm is illustrated in FIG. 5(c) and FIG. 6(a). The M dependence is almost the same as in the case where h 0.5 mm. However, when M becomes larger than an appropriate value, a noise component becomes larger than an original electric field component, and a high-frequency electric field distribution image is not formed. This suggests that a spatial resolution is restricted with an increase of h.

<h Dependence>

Subsequently, the h value (=hb) of the b (or B) function was changed and the influence thereof was examined. In actual observation using an live electrooptic imaging camera, there is a possibility that an error is added to measurement of a distance between the electrooptic crystal plate and the substrate surface, and thus a degree of hb dependence in the principle of the present invention is important information.

A window function was not used in a case where h=0.5 mm, and a window function of M=60 was used in a case where h=1.0 mm. The respective results are illustrated in FIGS. 5(b) and (d) and FIG. 6(b).

In a case where the hb value is smaller than the h value, the spatial resolution tends to degrade in accordance with divergence of the hb value. In a case where the hb value is excessive compared with the h value, a noise component increases. This clearly demonstrates that this principle is not merely an edge enhancement process and means that, in a case of actual application, an adjustment process for optimizing the hb value is necessary. This is considered to be similar to a process of adjusting a position of a sample with respect to an objective lens at the time of observation under a microscope. Anyway, the accuracy required of hb regarding the parameter in this case is about ±0.1 mm.

<Regarding Spatial Resolution>

From the above result, it turned out that the spatial resolution is improved by the present invention if an appropriate condition is set to hb and M. Also, it turned out that, in a case where h=about 0.5 mm or less, in which a situation of not being limited by M is realized, a result very close to the spatial resolution in a case where h=0 mm can be obtained.

The above discussion is given without considering the thickness of the electrooptic crystal plate. That is, an electrooptic crystal plate having a zero thickness is assumed. An actual live electrooptic imaging camera uses an electrooptic crystal plate having a finite thickness, and an integral effect in the z direction is generated inside thereof. The resolution can be further improved by modifying this influence. Conversely, the modification can be performed by calculating a height at which the resolution is optimized.

<Confirmation Through Experiments>

The effectiveness of DEI was verified by using an actual live electrooptic imaging camera.

<Experimental Device>

The experimental system illustrated in FIG. 1(a) was used. FIG. 1(b) illustrates the cross-section of the electrooptic crystal plate together with the holding mechanism. The electrooptic crystal plate has a thickness of 0.35 mm, but a protective plate composed of sapphire and having a thickness of 0.2 mm and a polyimide tape having a thickness of 0.07 mm are interposed between the electrooptic crystal plate and a sample. Here, the distance from the upper surface of the sample to the lower end of the polyimide tape is defined as h0.

<Result of Experiments>

Figure 7:
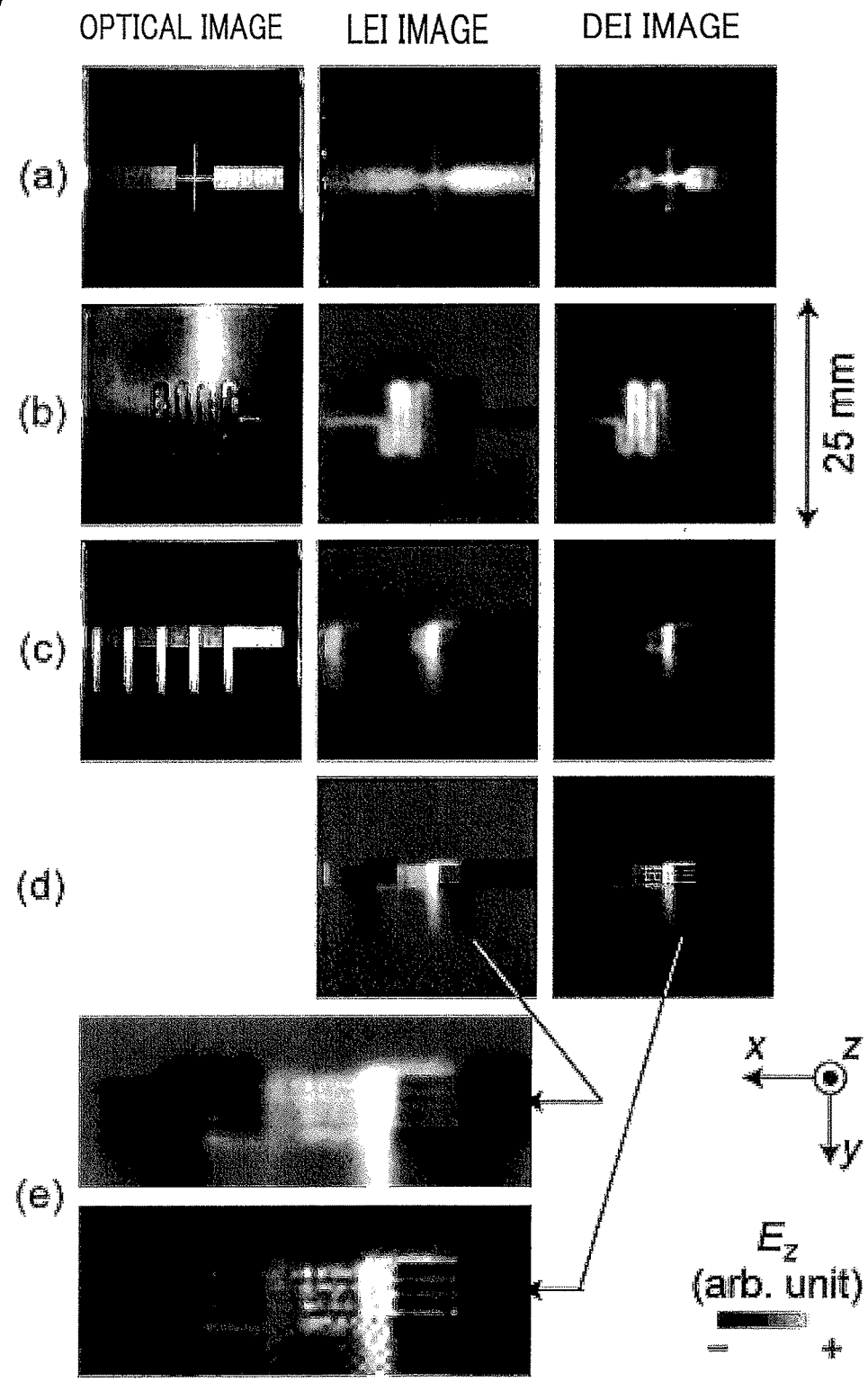
FIG. 7 is a diagram illustrating a result of experiments. (a), (b), and (c) respectively illustrate imaging results (LEI (live electrooptic imaging)) and DEI application results of propagation of a 2 GHz signal through a bandpass filter, a meander line, and a CRLH (composite right/left-handed) transmission line. The column of optical images includes CCD (charge-coupled-device) video images of surfaces of samples imaged through an ED (electrooptic) crystal plate, in which h0 in FIG. 1(b) is 0.5 mm. (d) illustrates a result in a case where h0=0 mm. (e) includes enlarged views of (d).

FIG. 7 illustrates a result of experiments. (a), (b), and (c) respectively illustrate imaging results (LEI) and DEI application results of propagation of a 2 GHz signal through a bandpass filter, a meander line, and a CRLH line. Any of them is a planar circuit and no part is mounted thereon. The column of optical images includes CCD video images of surfaces of samples imaged through an EO crystal plate, in which h0 is 0.5 mm. (d) illustrates a result obtained in a case where h0=0 mm. (e) includes enlarged views of (d).

Specific Example 1

As a result of trying various M values and hb values to search for a condition where the spatial resolution can be optimally improved, it turned out that M=35 and hb=0.75 mm correspond to h0=0.5 mm. As can be seen in FIG. 7(a) to (c), the spatial resolution is apparently improved. The cause of hb=h0+0.25 mm being an optimum condition is considered to be the holder structure of the electrooptic crystal plate in FIG. 1(b). The influence of the thickness of the electrooptic crystal plate is unknown.

Specific Example 2

Even under the condition where h0=0 mm, it is obvious from the above discussion that finite separation substantially exists between the electrooptic crystal plate and the upper surface of the sample. Thus, h0=0 mm is also a target of DEI. When DEI in which hb=0.25 mm was applied to the imaging result of the CRLH line, there was a definite improvement in the spatial resolution (FIG. 7(d)). The electric fields from individual comb-tooth electrodes arranged at an interval of 0.38 mm are clearly separated from one another.

In this way, a wiring layer surface or an electrode surface, or in a case where there is a dielectric layer covering these surfaces, a surface of the dielectric layer can be applied to the above-described surface.

Also, in a case where a part having a finite height is mounted on a circuit surface or in a case where an electrode is embedded in the circuit surface, a high-definition electric field video image can be obtained in real time, and it is obvious that the scope of application of the electric field imaging technique will significantly expand. The present invention enables high-definition imaging of a signal in a circuit mounted with a part, a three-dimensional circuit, an ultrafine circuit, or the like while suppressing invasion as much as possible, which was conventionally difficult, and also enables instantaneous high-definition imaging.

INDUSTRIAL APPLICABILITY

In a case of applying the present invention to a high-speed communication apparatus and network, a control circuit (motorcar, industrial machine, or the like), components used therein, and the like, it is expected that the time required to analyze or diagnose the operation, failure, EMI, or the like will be significantly shortened and the competitiveness will increase in terms of cost and performance.

A moving image used for displaying a temporal change in a high-frequency electric field distribution can be displayed similarly to an ordinary moving image, which is formed of still images that sequentially change and that are sequentially displayed. That is, a moving image of a high-frequency electric field distribution can be easily displayed by sequentially displaying images of the high-frequency electric field distribution that sequentially changes.

REFERENCE SIGNS LIST 1 object to be visually observed
2 electric field sensor
2a sapphire layer
2b electrooptic crystal plate
2c quartz crystal layer
2d polyacetal holder
2e polyimide tape
3 dichroic mirror
4 light source
5 CCD camera
6a, 6b polarization adjustor
7 polarization beam splitter
8 condenser lens
9 beam expander
10 optical LO source
11 imaging lens
12 image sensor
13 computer
14 local oscillator
15 high-frequency oscillator
16 amplifier
20 dielectric body
21 microstrip line
22 electrooptic crystal plate
31 electric field sensor+sensor signal processing unit
32 $E_Z$ image
33 window function W1
34 Fourier transform
35 (not described)
36 b function
37 Fourier space
38 division by B in Fourier space
39 window function W2
40 inverse Fourier transform
41 DEI image
42 display device
51 high frequency circuit
52 electric field sensor
53 sensor signal processing unit
54 image signal processing system
55 display means

The invention claimed is:

1. An electric field imaging method for detecting and imaging a two-dimensional distribution of a high-frequency electric field emanating from a high frequency circuit as an object to be visually observed (hereinafter abbreviated as a high-frequency electric field distribution), by using an electric field imaging apparatus including an electric field sensor, a sensor signal processing unit, an image signal processing system, and display means, comprising:

(1) detecting, by using the electric field sensor, a high-frequency electric field distribution at a position a predetermined distance away from a surface of the object to be visually observed;

(2) processing, by using the sensor signal processing unit, a signal from the electric field sensor to convert the signal to an image signal;

(3) in processing of the image signal using the image signal processing system, back-calculating, under an assumption that the high-frequency electric field distribution converted to the image signal in (2) is derived from a high-frequency electric field distribution at the surface of the object to be visually observed, the high-frequency electric field distribution at the surface from the detected high-frequency electric field distribution; and (4) displaying or outputting the high-frequency electric field distribution obtained through the back-calculating, thereby imaging an electric field distribution at a position closer to the object to be visually observed relative to the position at which the detecting is performed by the electric field sensor or at a position corresponding to the surface of the object to be visually observed, while suppressing disturbance to the object to be visually observed.

2. The electric field imaging method according to claim 1, wherein collective imaging of a high-frequency electric field distribution is performed by utilizing optical parallelism obtained by using an electrooptic crystal plate as the electric field sensor.

3. The electric field imaging method according to claim 2, wherein a Gauss' flux theorem is used in the back-calculating.

4. The electric field imaging method according to claim 1, wherein a Gauss' flux theorem is used in the back-calculating.

5. The electric field imaging method according to claim 1, wherein a distance at which a resolution of the high-frequency electric field distribution back-calculated from the detected high-frequency electric field distribution is optimum is used as the predetermined distance between the electric field sensor and the surface of the object to be visually observed in the back-calculating, thereby omitting inputting of a numerical value as the predetermined distance.

6. The electric field imaging method according to claim 1, wherein the high-frequency electric field distribution at the surface obtained in (3) is resolved into a spatial frequency spectrum after multiplied by a predetermined window function, filtered using a spatial spectrum filter having a predetermined filtering characteristic, and subjected to inverse Fourier transform so that a predetermined spatial frequency filtering is carried out.

7. The electric field imaging method according to claim 6, wherein the spatial spectrum filter has, at least at a high-frequency end, a spectrum reduction rate higher than an average in the spatial frequency spectrum.

* * * * *